United States Patent [19]

Rustick et al.

[11] Patent Number: 5,365,669
[45] Date of Patent: Nov. 22, 1994

[54] LASER BORESIGHT FOR THE SIGHTING IN OF A GUN

[76] Inventors: Joseph M. Rustick, 3043 E. Cyrpess, Phoenix, Ariz. 85008; Charles A. Finn, 2955 Cottingham, Oceanside, Calif. 92054

[21] Appl. No.: 996,088
[22] Filed: Dec. 23, 1992
[51] Int. Cl.⁵ .......................... F41G 1/54; G01B 11/27
[52] U.S. Cl. .......................... 33/234; 33/241lDIG. 21; 42/103
[58] Field of Search .................. 33/234, 241, 244, 286, 33/DIG. 21; 42/100, 103; 356/153

[56] References Cited

U.S. PATENT DOCUMENTS

| | | | |
|---|---|---|---|
| 2,773,309 | 12/1956 | Elliott | 33/234 |
| 2,889,629 | 6/1959 | Darkenwald | 33/244 |
| 3,510,965 | 5/1970 | Rhea | 42/103 |
| 3,782,832 | 1/1974 | Hacskaylo | 33/234 |
| 3,938,262 | 2/1976 | Dye et al. | 41/103 |
| 4,825,258 | 4/1989 | Whitson | 33/234 |
| 4,879,814 | 11/1989 | Wallace et al. | 33/234 |
| 4,976,038 | 12/1990 | Nattrass | 33/233 |
| 5,001,836 | 3/1991 | Cameron et al. | 33/234 |

FOREIGN PATENT DOCUMENTS 2161909  1/1986  United Kingdom ............... 33/234

*Primary Examiner*—Christopher Fulton
*Attorney, Agent, or Firm*—Joseph H. Roediger

[57] ABSTRACT

A boresight for determining the accuracy of a gunsight wherein a cartridge-shaped housing is dimensioned to fit within the gun chamber. A laser is contained in the housing. A switch is positioned in the end surface of the boresight housing to be contacted by the bolt face of the gun. The switch contains an indentation to receive the firing pin when the bolt face contacts the switch to activate the laser and illuminate a distant spot.

7 Claims, 1 Drawing Sheet

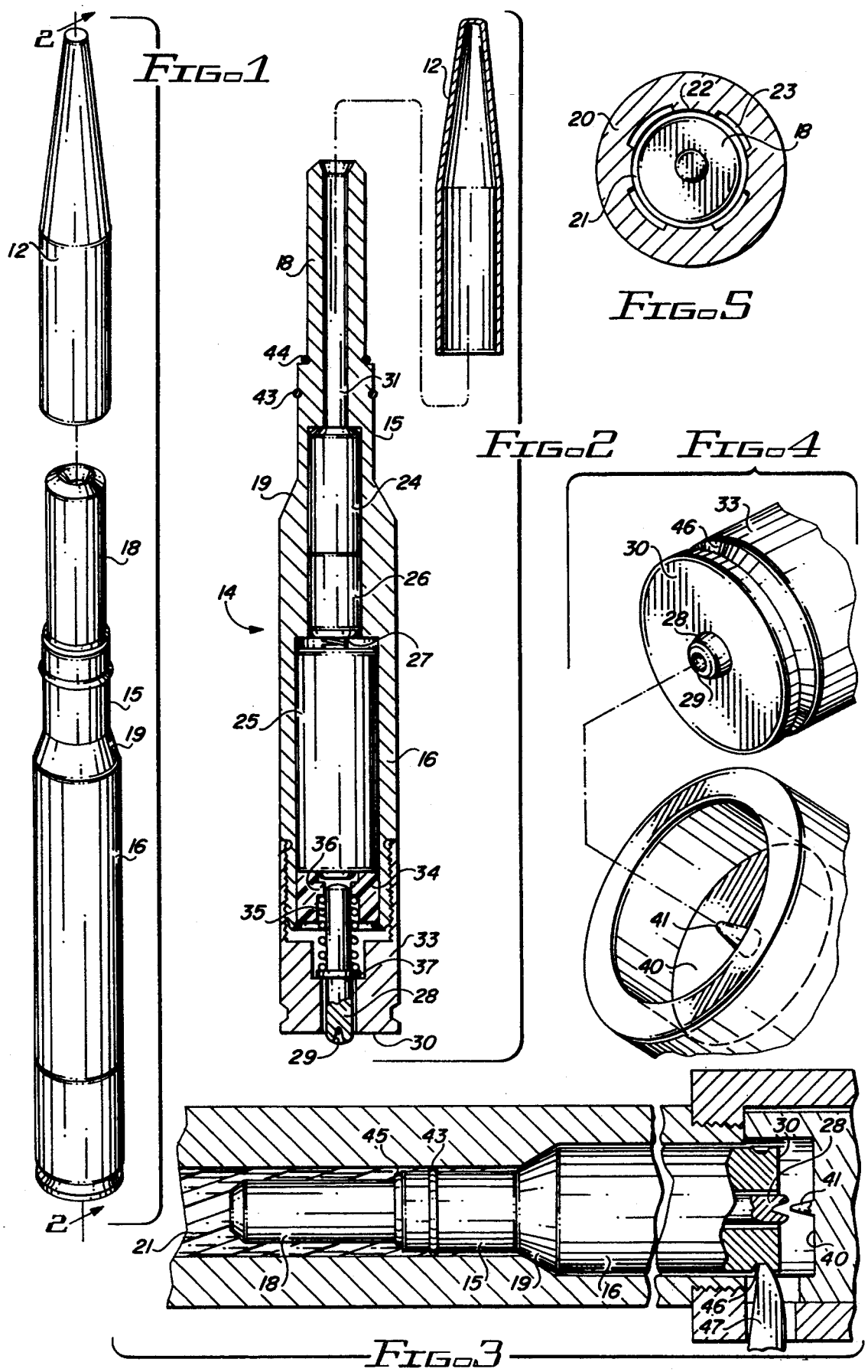

LASER BORESIGHT FOR THE SIGHTING IN OF A GUN

BACKGROUND OF THE INVENTION

This invention relates to a boresight for use in determining the accuracy of a sighting device affixed to a gun and, in particular, to a device utilizing a laser contained within a gun bore to illuminate the line of sight target location of the gun.

The conventional firearm contains a gunsight which may be either provided by the manufacturer as part of the weapon or later installed by the owner. The sighting-in of a gun is an important routine to be followed prior to use. The routine typically includes test firings followed by mechanical adjustment of the sighting device affixed to the gun. Adjustment based on the sighting-in process insures that the sighting device accurately foretells the line of sight direction of the gun bore. Considerable time is involved in travelling to a sighting facility and performing the particular sequence of steps utilized in the process.

In the case of the sensitive sighting devices which are increasingly being installed as optional equipment on guns, changing conditions experienced over a period of time can cause the sighting device to become misaligned. Consequently, periodic repetition of the sighting-in routine is a necessary part of the maintenance of a high accuracy gun. Furthermore, the special weapons available for use by tactical law enforcement units must be continually sighted-in due to the extraordinary circumstances in which they might be used.

The ability to verify the sight accuracy of a weapon under conditions that do not require firing the weapon enables one to perform the sighting-in operation at a location of his choice. More importantly, this ability enables the user to verify sight accuracy at the location where the weapon is intended to be placed in use. The performance of this process at the site results in a substantial saving in time and serves to increase the confidence level of the user. Furthermore, the ability to verify sight accuracy contemporaneously with use essentially eliminates changes and adjustments due to handling of the weapon during periods of non-use. Unrecognized misalignment of sighting devices affixed to guns has the potential for creating terrible consequences at a later time.

Accordingly, the present invention is directed to a boresight which enables a gun user to verify accuracy of a gunsight without requiring the gun to be fired. In addition, a gun user employing the present boresight can conduct a sighting adjustment and verification thereof contemporaneously with proposed use. The present invention utilizes the gun barrel and bore to create a line of sight target display for use in gauging the accuracy of the gunsight. The device is rugged, light in weight and easy to transport in a conventional cartridge belt.

SUMMARY OF THE INVENTION

This invention relates to a boresight which generates a line of sight display at a distant location by utilizing a collimated light source positioned within the gun bore. The location of the source within the bore duplicates the uncorrected path of a projectile from the gun barrel thereby establishing a distant reference for the sight affixed to the gun.

The present boresight permits a determination of the accuracy of the sighting device affixed to the gun to be performed at the site of perspective use and just prior to the actual use of the gun. No modifications to the gun are required in order to utilize the device. Thus, the gun includes the typical barrel with bore extending therethrough, a cartridge chamber and a movable bolt. The bolt contains a conventional bolt face with a firing pin positioned thereon so as to contact a cartridge located in the chamber and thereby initiate the firing reaction.

The present invention includes a housing having first and second end sections with a longitudinal axis extending therebetween. The housing is dimensioned to be received in the cartridge chamber of the gun. Thus, the device is an elongated tubular member manufactured to the dimensions of the particular type of gun with which it is to be used.

A collimated light source is mounted in the housing proximate to the first end section so that when energized, a collimated light beam is transmitted through the bore of the barrel. The housing contains a power source which is electrically coupled to the light source and to a switch means located in the second end section of the housing. The switch means is mounted in the second section so as to be actuated by contact with the bolt face when the firing sequence of the gun is carried out. The contact between the bolt face and a contact member of tile switch means activates the light source to illuminate a distant spot.

The spot displayed is located precisely in alignment with the line of sight through the bore of the barrel. The sighting device affixed to the gun is used concurrently to verify that it indicates that the line of sight of the bore coincides with the location indicated by the crosshairs or other indicia contained in the sighting device. Appropriate adjustment can then be made to bring the sighting device in registration with the distant spot projected by the boresight.

The second end section of the housing includes a strike surface which is contacted by the bolt face when the firing sequence, either single or double action as the case may be, is carried out. The switch means includes a contact member movably mounted in the second end section and extending outwardly from the strike surface. In order to prevent damage to the firing pin extending outwardly from the bolt face, tile contact member includes an indentation which accommodates or receives the firing pin therein when the bolt face moves toward the strike surface. Further, a biasing means is provided to urge the contact member beyond the strike surface of the housing so that the process can be immediately repeated without removing tile boresight from the gun chamber.

Further features and advantages of the invention will become more readily apparent from the following detailed description of a preferred embodiment thereof when taken in conjunction with the accompanying drawings.

BRIEF DESCRIPTION OF THE DRAWINGS

FIG. 1 is a perspective view of a preferred embodiment of the invention.

FIG. 2 is a side view in cross section of the embodiment of FIG. 1 taken along line 2—2 with the protective sleeve removed.

FIG. 3 is a side view in partial cross section of the embodiment of FIG. 1 positioned for use within a gun chamber.

FIG. 4 is a partial exploded view in perspective of the strike face and bolt face of the embodiment of FIG. 1.

FIG. 5 is an end view of a gun barrel containing the embodiment of FIG. 1.

DESCRIPTION OF THE PREFERRED EMBODIMENT

Referring now to FIG. 1, the elongated configuration of a preferred embodiment of the boresight is shown with the protective cover 12 spaced from the housing 14. The housing is configured to be received in the chamber of a gun for use in conjunction with the sighting-in of the sighting device affixed to the gun. Thus, the boresight dimensions are determined by the size of the chamber for the particular caliber gun with which it is to be used. The internal construction of the boresight is shown in the cross-sectional view of FIG. 2 which is taken along line 2—2 of FIG. 1.

The boresight includes a housing 14 which is divided into four sections. The first section 15 is connected to a hollow extension 18 at one end thereof and is joined by tapered region 19 to a second section 16. The configuration of the housing is determined by the caliber and make of the gun with which it is to be used. The boresight is chambered for use and actuated by the firing mechanism of the gun. The location of the tapered region 19 in relation to the strike surface and the degree of the taper is determined by the configuration of the chamber which is to receive the boresight.

The second section of the housing includes a threaded end cap 33 with a strike surface 30 at the end. Threaded end cap 33 is provided with a contact pin which actuates the device and extends outwardly of the strike surface 30. An indentation 29 is contained in the exposed end of the contact pin. A circumferential stop 37 is located on the pin and permits movement of the pin 28 along the longitudinal axis of the boresight. An insulating separator 34, typically machined from teflon, is provided with a pair of opposing recesses which communicate through a channel in which the inner end of pin 28 resides. The separator is located with in the second section 16. An actuating spring 35 surrounds the contact pin 28 and is positioned between the circumferential stop 37 and an internal projection 36 contained within separator 34. The fixed internal-projection 36 and the spring 35 provide a biasing force exerted against the circumferential stop which urges the pin 28 to a normal position wherein the contact pin extends from the strike surface 30 as shown.

Battery 25 is contained within the second section 16 of the housing and is axially aligned so that the center electrode thereof is positioned to contact pin 28 when it is urged into the housing. The insulating separator 34 has a centrally located recess to receive the battery electrode. Thus, the insulating separator maintains the axial alignment of the pin with the center electrode and also provides the fixed support for the biasing spring 35. At the opposing end of battery 25 is a conductive buffer spring 27, preferably secured to one end of a cylindrical laser 26. Laser light sources of this type are commercially available. A laser which emits visible red light is used in the embodiment shown in FIG. 1. A protective ferrule 24 surrounds the light emitting end of the laser 26 in the embodiment shown. However, a protective ferrule is not necessary for use in connection with cylindrical lasers having an outer protective casing. The end of the protective ferrule rests against the shoulders provided by bore 31. The light emitted by the laser is a collimated beam of light which exits the boresight through the bore 31 to illuminate a distant spot. This spot provides the line of sight reference for adjustment of the sighting device affixed to the gun. The protective sleeve 12 is shown in FIG. 2 removed from the hollow extension 18. During storage, this sleeve is placed on the extension and is retained by urging its open end over the retention O-ring 44 contained in circumferential groove on the outer surface of extension 18.

The embodiment of FIG. 1 is shown in operating position in the chamber of a gun in FIG. 3. The gun bore 21 contains the hollow extension 18 of housing 14 and is made smaller in diameter than first section 15 to provide a degree of clearance of either side thereof. The retention groove 45 is shown at the juncture of the hollow extension 18 and the first section 15 with the retention O-ring 44 removed. The boresight is inserted in the chamber with the tapered region 19 establishing its position against the corresponding tapered surface of the chamber. The outer dimensions of the first section 15, the tapered region 19 and the second section 16 are made equal to the corresponding dimensions of the cartridge normally used with this type of gun. A stabilizing O-ring 43 is located in a receiving groove formed on the outer surface of the first section 15. The stabilizing O-ring is used in the preferred embodiment to insure that the source of collimated light is fixedly positioned within the chamber and that movement in relation to tile gun does not occur during use.

At the opposing end of the boresight, the contact pin is shown extending beyond the plane of the strike surface 30 with the indentation therein in alignment with the firing pin 41. The bolt face 40 of the gun is shown in its pre-actuation position. The completing of the firing sequence for the gun will advance the bolt face 40 against the exposed end of the contact pin so as to come to rest next to the strike surface. The firing pin is totally received in indentation 29 so that it is not damaged by use of the boresight. When the bolt face is in the firing position, the force of the bolt face overcomes the bias of actuating spring 35 and the contact pin rests against the adjacent electrode of the battery 25. To insure that there is no damage to the laser 26 by virtue of movement along the longitudinal axis of the battery, the buffer spring 27 absorbs and compensates for any force applied to the battery.

The relationship between the bolt face 40 and firing pin 41 thereon to the strike surface 30 with its centrally located contact pin 28 is shown in the exploded view of FIG. 4. The centrally located indentation 29 receives the conical firing pin 41 therein. A circumferential ejection groove 46 is located in the second section of the boresight housing and is axially spaced from the strike surface 30. The circumferential groove 46 is provided to receive all ejection pin 47 as shown in FIG. 3. The ejection pin facilitates removal of the boresight after completion of the sighting-in process. The end view of FIG. 5 shows the boresight in position within the bore 21 of gun barrel 20. The lands 22 and grooves 23 formed within the barrel surround the housing of the boresight with the lands being spaced from the hollow extension 18.

In operation, the boresight is placed in the chamber of the weapon and is received therein as if it were a conventional cartridge position for firing. The firing sequence for the gun is carried out and a collimated beam of light exits the bore of the gun barrel to illuminate a distant spot. The user observes the location of that spot in the sighting device of the gun and can make appropriate corrections to insure that the sighting device properly indicates the line of sight from the gun bore. The boresight is then ejected from the gun by utilization of the particular ejection means provided. A cartridge can then be inserted and the gun fired from the same location. Thus, the present invention provides a device for carrying out the sighting-in of a gun at the site in which the gun is proposed to be used. Furthermore, the laser need not emit in the visible portion of the spectrum, but may be used in combination with night vision or other goggles to illuminate a spot with light from outside the visible portion of the spectrum. As a result, sighting-in can occur right on the proposed target without observation by others.

While the foregoing description has been with reference to a particular embodiment of the invention, it is to be noted that many modifications and variations may be made therein without departing from the scope of the invention as claimed.

We claim:

1. A boresight for determining the accuracy of a sighting device affixed to a gun, said gun including a barrel, a cartridge chamber and a bolt having a bolt face with a firing pin positioned thereon, said boresight comprising:
   a) a housing having first and second sections with a longitudinal axis extending therebetween, said housing including a tapered region intermediate said first and second end sections, said tapered region being dimensioned to conformabl(e)y contact the cartridge chamber and limit axial movement therein;
   b) an end cap removably affixed to the second end section, said end cap having a centrally-located opening therein;
   c) stabilizing means mounted on the first end section, said stabilizing means contacting the barrel when said boresight is inserted therein;
   d) a collimated light source mounted in said housing proximate to the first end section thereof, the energization of said light source transmitting collimated light through the barrel;
   e) a power source contained within said housing and electrically coupled to said light source; and
   f) switch means electrically coupled to said power source and located in the second end section of said housing, said second end section and extending outwardly from said opening in the affixed end cap for contact with the firing pin(.) said contact member having an indentation therein to receive said firing pin.

2. The invention in accordance with claim 1 further comprising buffer means positioned between said light source and said contact member for absorbing force transmitted by movement of said contact member.

3. The invention in accordance with claim 2 wherein said housing includes a hollow extension affixed to the first end section and axially aligned therewith.

4. The invention in accordance with claim 3 further comprising a protective sleeve removably attached to said extension.

5. The invention in accordance with claim 4 further comprising retention means located on said extension for securing the protective sleeve thereon.

6. The invention in accordance with claim 1 wherein said switch means includes a biasing means for urging the contact member outwardly from the end cap.

7. The invention in accordance with claim 6 wherein said end cap contains a circumferential groove for facilitating removal of the boresight from the chamber.

* * * * *

UNITED STATES PATENT AND TRADEMARK OFFICE
CERTIFICATE OF CORRECTION

PATENT NO. : 5,365,669
DATED : November 22, 1994
INVENTOR(S) : Joseph M. Rustick
Charles A. Finn It is certified that error appears in the above-identified patent and that said Letters Patent is hereby corrected as shown below:

Col. 5, lines 27-33, claim 1, subparagraph a) should read:

a) a housing having first and second sections with a longitudinal axis extending therebetween, said housing including a tapered region intermediate said first and second end sections, said tapered region being dimensioned to conformably contact the cartridge chamber and limit axial movement therein; and Col. 6, lines 10-16, claim 1, subparagraph f) should read:
In Claim 1, subparagraph f) should read:

f) switch means electrically coupled to said power source and located in the second end section of said housing, said switch means including a contact member movably mounted in said second end section and extending outwardly from said opening in the affixed end cap for contact with the firing pin said contact member having an indentation therein to receive said firing pin.

Signed and Sealed this

Twenty-eight Day of March, 1995

Attest:

BRUCE LEHMAN

Attesting Officer    Commissioner of Patents and Trademarks